(12) United States Patent
Portney (10) Patent No.: US 9,931,203 B2
(45) Date of Patent: Apr. 3, 2018

(54) PRESBYOPIA CORRECTING WIRELESS OPTICAL SYSTEM

(71) Applicant: Valdemar Portney, Newport Coast, CA (US)

(72) Inventor: Valdemar Portney, Newport Coast, CA (US)

(*) Notice: Subject to any disclaimer, the term of this patent is extended or adjusted under 35 U.S.C. 154(b) by 0 days.

(21) Appl. No.: 14/642,236

(22) Filed: Mar. 9, 2015

(65) Prior Publication Data
US 2015/0173893 A1 Jun. 25, 2015

Related U.S. Application Data

(60) Continuation-in-part of application No. 14/082,039, filed on Nov. 15, 2013, now abandoned, which is a
(Continued)

(51) Int. Cl.
*A61F 2/16* (2006.01)
*A61F 2/14* (2006.01)
(Continued)

(52) U.S. Cl.
CPC .......... *A61F 2/1654* (2013.01); *A61F 2/142* (2013.01); *A61F 2/145* (2013.01); *A61F 2/1635* (2013.01); *G02C 7/04* (2013.01); *G02C 7/085* (2013.01); *A61F 2250/0002* (2013.01); *A61F 2250/0004* (2013.01); *G02C 2202/20* (2013.01)

(58) Field of Classification Search
CPC ...... A61F 2/1654; A61F 2/142; A61F 2/1635; A61F 2250/0004; A61F 2/1627; A61F 2250/0009; A61F 2250/001; A61F 2250/0013; A61F 2250/0091; G02C 7/085; G02C 2202/06
See application file for complete search history.

(56) References Cited

U.S. PATENT DOCUMENTS 8,348,422 B2 1/2013 Pugh et al.
8,574,295 B2 11/2013 Roholt
(Continued)

FOREIGN PATENT DOCUMENTS

EP 2 687 898 A1 1/2014
WO 2010 003058 A2 1/2010

*Primary Examiner* — Paul Prebilic
(74) *Attorney, Agent, or Firm* — Hackler Daghighian Martino & Novak (57) ABSTRACT

An optical accommodating system for an eye includes a sensor assembly and an adjustable optic assembly. The sensor assembly includes a sensor configured to sense a movement of the ciliary muscle and produce a signal, an electronic processor, a transmitter and a power source. The adjustable optic assembly is configured to be either implanted within or on the eye, or configured to be disposed adjacent to or near the eye. The adjustable optic assembly includes a switchable optical lens assembly configured to change its optical power between a first state and a second state, a receiver configured to receive the transferable signal from the transmitter of the sensor assembly, a second electronic processor connected to the receiver which directs the switchable optical lens assembly to change its optical power between the first state and second state, and a second power source connected to the second electronic processor.

14 Claims, 6 Drawing Sheets

Related U.S. Application Data division of application No. 13/247,840, filed on Sep. 28, 2011, now Pat. No. 8,608,800.

(60) Provisional application No. 61/514,413, filed on Aug. 2, 2011, provisional application No. 61/950,942, filed on Mar. 11, 2014, provisional application No. 61/984,954, filed on Apr. 28, 2014, provisional application No. 62/027,123, filed on Jul. 21, 2014.

(51) Int. Cl.
*G02C 7/08* (2006.01)
*G02C 7/04* (2006.01)

(56) References Cited

U.S. PATENT DOCUMENTS

| | | | | |
|---|---|---|---|---|
| 8,608,800 B2 * | 12/2013 | Portney | | G02C 7/04 351/159.11 |
| 8,778,022 B2 | 7/2014 | Blum et al. | | |
| 8,857,983 B2 | 10/2014 | Pugh et al. | | |
| 9,351,827 B2 * | 5/2016 | Toner | | G02C 7/04 |
| 2010/0331977 A1 * | 12/2010 | Schaper, Jr. | | A61B 5/04001 623/6.37 |
| 2013/0035760 A1 * | 2/2013 | Portney | | G02C 7/04 623/6.13 |
| 2013/0184815 A1 * | 7/2013 | Roholt | | A61F 2/1635 623/6.22 |
| 2013/0190867 A1 * | 7/2013 | Peyman | | A61F 2/1635 623/6.13 |
| 2013/0194540 A1 * | 8/2013 | Pugh | | A61F 2/1635 351/159.03 |
| 2013/0211514 A1 | 8/2013 | Peyman | | |
| 2013/0261535 A1 * | 10/2013 | Behar-Cohen | | A61K 41/0028 604/22 |
| 2013/0282117 A1 | 10/2013 | Van Heugten et al. | | |
| 2014/0085726 A1 | 3/2014 | Portney | | |
| 2014/0156000 A1 | 6/2014 | Campin et al. | | |
| 2014/0232982 A1 | 8/2014 | Iwai | | |
| 2014/0243971 A1 * | 8/2014 | Pugh | | G02C 7/04 623/6.22 |
| 2015/0272727 A1 * | 10/2015 | Humayun | | A61F 2/1635 623/6.39 |

\* cited by examiner

PRESBYOPIA CORRECTING WIRELESS OPTICAL SYSTEM

CROSS-REFERENCE TO RELATED APPLICATIONS

The present application is a continuation-in-part of application Ser. No. 14/082,039 filed on Nov. 15, 2013, now abandoned, which was a divisional application of application Ser. No. 13/247,840 filed Sep. 28, 2011 now U.S. Pat. No. 8,608,800 issued on Dec. 17, 2013, which itself claimed priority from provisional application 61/514,413 filed Aug. 2, 2011. The present application also claims priority to provisional patent application 61/950,942 filed on Mar. 11, 2014, provisional application 61/984,954 filed on Apr. 28, 2014 and provisional application 62/027,123 filed on Jul. 21, 2014. The entire contents of all the applications mentioned herein are hereby incorporated by reference in their entirety.

DESCRIPTION

Field of the Invention

The present invention relates generally to a sensor interacting with ciliary muscles that transmits a signal to an ophthalmic lens to change its optical power between far and near foci. More particularly, the present invention relates to the sensor cell that responds to pressure or electric field change with ciliary muscles contraction or and relaxation with accommodation and disaccommodation, and to transmit data corresponding to accommodation or disaccommodation to activate an ophthalmic adjustable lens for switching between far and near foci. The present invention also relates to the system of wireless communication between a sensor cell that responds to pressure or electric field change by ciliary muscles contraction and relaxation with accommodation and disaccommodation for communication with dual-chamber adjustable ophthalmic lens activated by electrostatic force for switching between far and near foci.

Background of the Invention

The present application incorporates the description of refractive-diffractive switchable optical element disclosed in the U.S. Patent Application Publication No: 2014/0085726.

The anatomy of ocular elements involved in human eye accommodation is illustrated by FIG. 1 of application Ser. No. 13/247,840 filed Sep. 28, 2011. The ciliary muscles play central role in eye accommodation. They are triangular in cross-section of ≈4.5-5.2 mm nasally and 5.6-6.3 mm temporally. The ciliary muscles are a part of the ciliary body that is circumferential to the iris. The ciliary body has three basic functions, (a) aqueous production and removal through the trabecular meshwork to collect it in Schlemm's canal, (b) accommodation, and (c) formation of vitreous mucopolysaccharide (it acts like binding, lubricating element). Accommodation function is the central subject of the present invention and ciliary muscles confined by the ciliary body play central role in this function.

The ciliary muscles consist of longitudinal, radial, and circular muscles fibers. The greater part of ciliary muscles is composed of longitudinal fibers running anterior-posterior (front-to-back) on the inner aspect of the sclera (outer layer of the eye called white of the eye) about 8 mm behind the limbus (border of the cornea as transparent part of the eye and sclera. Posteriorly, the longitudinal fibers are attached by tendinous insertions to the elastic choroid. At the front, the longitudinal fibers are attached to the scleral spur.

Accommodation is the ability of eye to focus on far and near objects without an optical aid. Near vision occurs with ciliary muscle contraction that changes ciliary body shape with the help of elastic choroid and scleral spur both acting as muscle anchors in the eye. Far vision (disaccommodation) occurs with ciliary muscle relaxation also with the help of elastic choroid and scleral spur. Thus, the area in and at the ciliary muscles around a scleral spur is: (a) active area during accommodation/disaccommodation in terms of ciliary muscles actions and (b) accessible for a surgical procedure as being likely a minor modification of already well developed glaucoma surgical procedure such as glaucoma shunt installed close to trabecular meshwork.

Application Ser. No. 14/082,039 described a sensor cell device implanted at the anterior of the ciliary muscles of an eye close to the scleral spur to harvest pressure changes by ciliary muscles contraction and relaxation for near and far foci. The described sensor cell was acting as a pressure sensor.

There is a significant effort to develop an adjustable lens for presbyopia correction that changes eye optical power under the action of ciliary muscles. Presbiopia condition is generally defined as the inability to see at far and near distances without an optical aid where far is commonly defined as a distance of 4 meters and beyond from the eye and near is a distance of 50 cm and closer to the eye with a distance in between is referenced to as intermediate distance. The presbyopia develops due to inability of a natural crystalline lens to change its shape for its optical power change between far and near foci. A use of wireless communication between a device that harvests input from ciliary muscles to control power change of an adjustable lens for presbyopia correction is the subject of the present invention.

Different types of radio-frequency (RF) communication can be used between the Sensor Cell and adjustable optic (NFC, Bluetooth, Wi-Fi, etc.) but Near Field Communication (NFC) is likely preferable one. NFC is a technology that allows the transfer of small amounts of data via radio frequency identification (RFID) transponders between various types of devices. NFC uses magnetic induction between two loop antennas (transponder and target) located within each other's near field (reading distance), effectively forming a transformer. NFC operates within the globally available and unlicensed radio frequency ISM band (as opposed to where additional security is required over traditional RFID tag) due to a very short reading distance, typically 10 cm or shorter but may be up to about 20 cm with a weaker interaction. The corresponding reading distance is adequate for communication by only one implanted sensor cell with adjustable lenses at both eyes in bilateral placement and, at the same time, to minimize interference from other external devices.

Near field RFID uses magnetic induction between a reader and a transponder. If an RFID tag (transponder) is placed within range of the reader, the alternating voltage appears across it and the magnetic field is affected by data stored on the tag. The voltage is rectified and powers the tag. As it is powered, the data are sent to the reader.

In terms of terminology and advantage of NFC besides a short communication range. There is "Reader mode" allowing the NFC-enabled device to read a RFID tag (transponder) and "P2P mode" allowing the NFC-enabled device to exchange information with other NFC-enabled device. An NFC-enabled device may also "write" data into a RFID tag. NFC Interaction is based on a message/reply system. A device that begins the interaction process is called the "initiator" and the other called the "target". NFC-enabled device A as initiator sends a message to a NFC-enabled device B as a target, device B then responds as the device B cannot send data without being contacted first by the initiator (device A). The important advantage is that NFC forgoes the "pairing" process between NFC-enabled devices entirely contrary to other M2M technologies (Bluetooth, Wi-Fi) though other wireless technology can also be applied in the present invention. Thus, NFC-enabled device allows automatic "pairing" and effortless communication and control of data transfer.

In terms of a power source to power the sensor cell and adjustable lens there are two types of power supply: micro batteries or radio-power transmission by inductance. Thin-film micro batteries are composed of successive sub-micron to several micron-thick layers of cathode ($LiCoO_2$ or $LiMn_2O_4$), lithium phosphorus oxynitride (LIPON) electrolyte and a lithium or silicon tin oxynitride anode. Planar batteries have cathodes with thicknesses of up to 5 micron and might be applicable for a sensor cell in rechargeable form by inductance. An adjustable optic might be powered by photocell because accommodation is not required at low light condition, specialized micro battery or by inductance from the sensor cell. In short, multiple power solutions are possible.

There are a number of publications that disclosed wireless communication with ophthalmic lens. The U.S. publication No: 2014/0232982 by Iwai describes dynamic multifocal contact lens with two transparent layers with optical fluid in between and each with annular electromagnet. Upon initiation by a user, a remote transmitter signals the loop antenna for near field communication to energize the electromagnets for a mutually attracted configuration causing the fluid redistribution and the central portion of the first layer to deform into a second shape of higher power. A remote transmitter in this case is either manual or detecting a change in gaze of the eye. An inclusion of electromagnet is fairly complex and involves a current flow to create a magnetic field which is an additional safety issue.

The U.S. Pat. No. 8,348,422 by Pugh describes an apparatus for activating an energized ophthalmic lens. The patent describes components involved in wireless communication and mentions an energized lens but does not describe such a lens in detail in terms of structural changes of the lens for a vision enhancement.

The U.S. Pat. No. 8,574,295 by Roholt describes a compressible accommodating intra-ocular coupled to the ciliary sulcus ring sensor such as an electromyographic receiver which detects a signal created by the ciliary muscle. The sensor includes miniaturized electrodes for implanting into the ciliary muscle of the subject and a microcomputer modulates the ciliary muscle signal detected by the sensor(s) into an electrical signal for transmittance to a micromotor, which causes compression of the IOL via an annular support ring system to change lens power. A placement of the sensors at the ciliary ring creates an uncertainty with the ciliary muscle electrodes position and quality of signal. There is uncertainty with a depth of the electrodes and also an eye sulcus diameter varies. This is additional uncertainty between the individual differences with signal characteristics which has not been addressed. Another complexity is the use of micromotor to compress the lens for optical power change.

U.S. Pat. No. 8,778,022 by Blum shows a stabilized electro active lens which can be remotely programmed. This patented lens includes an electro active element and a view detector. The electro-active element provides vision improvement to the user upon supply of an electric charge. The element may include polymer gels, liquid crystals, pixilated grid elements, transparent electrodes and insulators, and similar devices The U.S. Pat. No. 8,857,983 by Pugh describes an ophthalmic lens consisting of a die structure of layers with mounted on one of them electronic components that includes antenna for electro-magnetic communication and inductive coupling for energy charging. The electronic arrangement is described for a general lens use such as data to be transmitted or received may include tear film analysis, intra ocular pressure, heart rate, blood pressure, to sense ciliary muscle contraction for an accommodating lens and like without disclosing a specific sensor mechanism for providing such data. There is no a description of a specific mechanism of an ophthalmic lens for changing its structure for accommodation and other optical characteristic except a reference to the die structure of layers.

The U.S. Patent Application Publication 2014/0156000 by Campin describes electromyography sensor to detect an electric field in a ciliary muscle of the eye that is proportional to a force exerted by the ciliary muscle and to generate a sensor signal indicative of the electric field. The application states that rather than detecting a binary transition between near and far vision, such a system could allow a continuous range of adjustment correlated to the electrical activity of the ciliary muscle tissue, which can in turn be calibrated based on the observed accommodation demand. Such calibration could be based on an average response in the population; alternatively, the calibration could be patient-specific. The publication described a number of difficulties for continuous communication without providing descriptions how to reduce the described concepts to practice. The publication hasn't described a specificity of a sensor positioning and supporting it in or on the eye and being more on a conceptual level. This is additional uncertainty between the individual differences with signal characteristics which has not been addressed and a definition of calibration. The ciliary muscles mechanics is a complex system and it would be desirable to achieve a continuous focus from far to near but such a system presents the immense difficulty which has not been addressed by the application.

Though a wireless communication has been used before, its proper and practical application to a biological system and particularly to presbyopia correction is lacking. There is no a disclosure for an individual implementation as an interaction between a sensor and ciliary muscles may vary widely between the subjects and may also change in time for a given subject.

Another deficiency is the absence of systemic approach, the disclosures either describe a communication between a sensor and a lens in general terms without a specific explanation how the communication is reduced to the actual presbyopia correction or an implementation of the sensor is rather questionable in terms of its position inside the eye.

There are multiple issues which have not been addressed by prior arts: (1) ciliary muscles structure is complex and depending upon sensor cell location, the signal detecting their actions can vary significantly; (2) some disclosures mentioned signal calibration without explaining what it actually is; (3) even if a calibration of some sort is performed, it must be done with an adjustable lens in place leading to another complication that the surrounding of the lens is also not fixed as any biological system potentially leading to re-calibration; (4) adjustable lenses are likely implanted binocularly and calibration of the sensor for one lens might not be applicable for another lens unless two sensor cells are installed individually for each lens which is highly undesirable. On the other hand, if adjustable lenses have to be calibrated, it would evolve more complex structure and cost of the adjustable lenses. A disclosure how to handle these critical issues is absent in all prior arts of wireless communication applications to ophthalmic lenses thus leaving a need for a relatively simple and effective arrangement between sensor cell and adjustable lenses.

Thus, it would be desirable to provide methods and devices which address the above deficiency and weaknesses for practical application of wireless technology to sensor cell to communicate ciliary muscles states of contraction and relaxation.

It still further would be desirable to provide methods and devices for implementation communication from the sensor cell for presbyopia correction in conjunction with adjustable lens that is simple in construction and safe and effective in the application.

SUMMARY OF THE INVENTION

Generally, a sensor cell may be implanted at any part of the ciliary muscle for its mechanical (pressure) or/and electromyographic (EMG) interaction with them via mechanical (pressure) probe(s) or electrical field by EMG electrod(s) but it is more practical to apply it to the area around the scleral spur. A sensor cell incorporates electronic processing to transfer a signal from the pressure probe or EMG electrode into usable electric signal which involved digitization, amplification and processing. A sensor cell also incorporates a microchip for wireless transmission of the processed electric signal into the electro-magnetic wave to communicate with an adjustable optic. It includes a pairing or initiation signal to recognize the adjustable lens before sending a signal for the lens activation for optical power change. A wireless communication is used such as Near Field Communication (NFC) or Super Bluetooth or any other wireless technology though it is preferably to utilize a short range communication such as NFC due to its advantages.

It might be desirable for the sensor to include several pressure probes at different parts of the sensor that can be located at the opposite sides of the muscles at the scleral spur area in order to improve a quality of signal. It may also be advantageous to include the interaction with different muscle fibers to improve the quality of signal.

Similar to a pressure sensor, in order to extract useful information from the signal of EMG sensors, the signal is electronically transformed into a more meaningful form such as a digital signal representation, which can be amplified it to enable analysis. Placement of pressure sensor with its pressure probe(s) and EMG sensor with its electrode(s) is important. For instance, it is desirable in case of EMG sensor for instance, to place several electrodes along the imaginary line that joins them to be parallel to the muscular fiber orientation, i.e. front-to-back of the eye if interacting with longitudinal fibers or perpendicular to front-to-back line if considering radial fiber.

The central part disclosed by the present invention involves signal identification. Upon a sensor cell installation, the signal generated by the sensor during stimulation by the ciliary muscles contraction and relaxation is recorded. During the same stimulation the actual visualization of ciliary body contour change during ciliary muscles contraction and relaxation is also recorded by, for instance, by high frequency ultrasound biomicroscopy (UBM) to insure that stimulation actually results in ciliary muscles contraction and relaxation to avoid faults signals. This is a very critical aspect in dealing with accommodation which has not been addressed in prior arts.

The sensor cell signal is digitized, processed and filtered and the next step is to convert the signal into identification signals associated with ciliary muscles states, i.e. contraction and relaxation, though it is also possible to have ciliary muscles states identification for 3 states—contraction, relaxation and in-between. The process involves time synchronization between the sensor cell signal and ciliary body visualization signal. The visualization signal is divided into ranges associated with the relaxation state and contraction state and the convertor transforms the timed synchronized ranges of sensor cell signal associated with the selected visualization range of relaxed muscles into the convertor data for relaxation state, say signal "1", and the sensor cell signal associated with the selected range of contracted muscles into the convertor signal for contraction state, say signal "0". The process is called the sensor cell ciliary muscle identification for ciliary muscle states and corresponding identification data are transmitted to the adjustable optic. No need for signal calibration which is an unreliable process anyway. As the adjustable lens receives the signal "1", it changes its optical condition to far focus and if it receives the signal "0", it changes its optical condition to near focus. In case of identification of 3 states, i.e. also in-between identification for intermediate by the corresponding signal "2", the adjustable lens takes the optical condition for intermediate focus. This is so called communication by the identification data.

Transmission of the ciliary muscle identification data (CMID) instead of a signal directly generated by the sensor cell, though electronically processed, provides a reliable communication with an adjustable lens or multiple adjustable lenses. It is not always required for an adjustable lens to continually respond to a signal and only respond to its change from "1" to "0", i.e. for switching from far to near focus, or from "0" to "1", i.e. for switching from near to far focus, thus reducing a power consumption of the adjustable lens.

Some additional explanation of the identification data communication is taught herein. All of the prior art references teach an analog communication between the transmitter of the sensor cell and the receiver of the adjustable optic, i.e. as the signal from the sensor increases, the receiver via the processor changes the optical state of the adjustable optic accordingly. As a result, they need some sort of calibration to establish a correlation between the action (sensor cell interaction with muscles) and reaction (adjustable optic power state change). The "calibration" is very uncertain and likely difficult. The embodiments disclosed herein avoids such complexity by introducing identification data, which is a digitized correlation between action (sensor cell interaction with muscles) and reaction (adjustable optic power state change). The establishing identification data involves analyzing the actions of the ciliary muscles in terms of establishing that a certain range of the muscle's change is defined as "muscles contraction" and another range of ciliary muscle's change is defined as "muscles relaxation". This is done based upon scientific knowledge of the ciliary muscle's actions and the individual patient upon the placement of the sensor cell in the eye. Then, it involves recording the sensor cell signal ranges corresponding to the "muscles contraction" and "muscles relaxation" ranges and then programming electronically and assigning identification data to the corresponding range of sensor cell signal. Thus, the processor of the sensor cell is programmed to transmit identification data instead of a sensor sell signal. It means if a sensor cell signal is within the range corresponding to the "muscles contraction", the sensor cell transmitter transmits the identification data, say, "1" and if within the range of "muscles relaxation" the transmitted identification data is "0". As long as an adjustable optic (any type, not just dual-chamber fluidic lens) receives identification data "1" it changes to a higher optical power, and if identification data "0" is received it changes to a lower optical power. Thus, there is no need for a calibration. This is also beneficial for binocular implantation of adjustable optics as a calibration of the prior art might be difficult due to different locations of the adjustable optics, but in case of the identification data both adjustable optics acts the same way.

The present invention has also addressed a question of securing communication between a given sensor cell with corresponding adjustable optic. This is to avoid an inadvertent communication of the adjustable optic with a different censor cell or even other wireless devices. For this purpose the sensor cell ID is used to establish unique recognition of the signal between the sensor cell and adjustable optic.

The present invention has also addressed a question of bilateral placement of adjustable lenses for right and left eyes and ciliary muscle action during accommodation. Accommodation is commonly equivalent between the eyes and only one sensor cell implantation is required to control bilateral placement of adjustable optic lenses with the introduction of identification data. Similar as above, sensor ID is used to establish unique communication with both adjustable optics by programming the ID into their RFID tags.

The present invention also discloses dual-chamber electrostatically activating fluidic lens as a desirable option for a wireless system that includes a sensor cell that responds to ciliary muscles contraction and relaxation for the signal transmission to the adjustable lens. There is also an advantage to apply specific type two-chamber fluidic switchable lens that was disclosed in the U.S. Patent Application 2014/0085726 entitled "Refractive Diffractive Switchable Optical Element". This type of adjustable lens acts as opto-mechanical transistor where the optical powers for far and near foci are set by the lens design itself. The corresponding optic is called RDS optic and it allows a reduction of necessary processing power because it is inherently digital by design due to switching between preset far and near foci if a signal is below set threshold or above it. It also reduced power consumption as the power is used only to change to preexisting optical power state of the RDS optic without a need to continually control the optical power state of the lens.

Features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figures 1, 2:
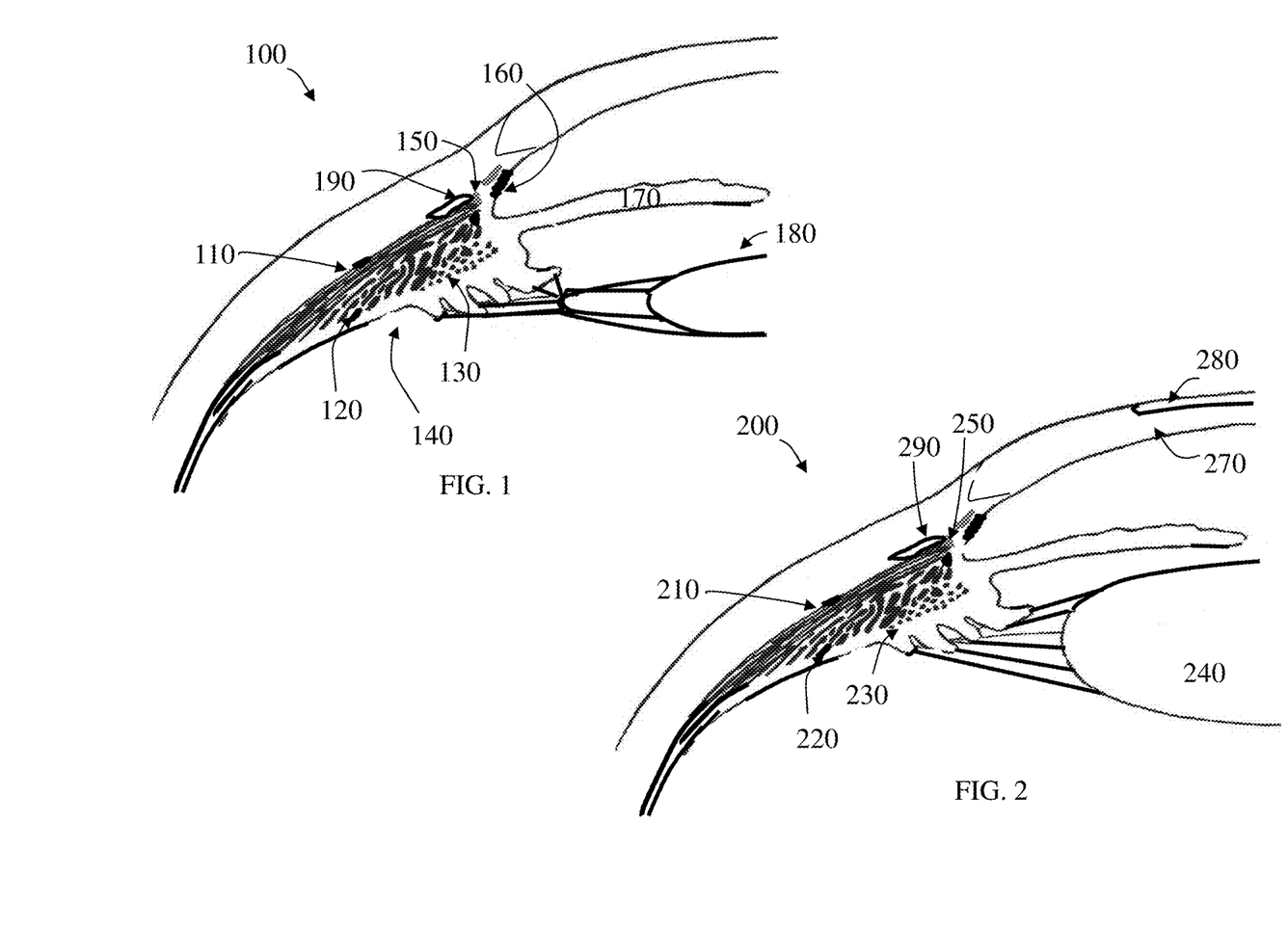
FIG. 1 illustrates a portion of eye anatomy responsible for the accommodation process with implanted aphakic intra-ocular lens and sensor cell at the exterior of longitudinal fibers at the vicinity of the scleral spur.
FIG. 2 illustrates a portion of eye anatomy responsible for the accommodation process with implanted corneal implant (inlay) and sensor cell at the exterior of longitudinal fibers at the vicinity of the scleral spur.

FIG. 1 illustrates a portion 100 of eye anatomy responsible for the accommodation process shown as the eye's cross section. The FIG. 1 includes implanted aphakic intra-ocular lens 180 that replaces natural lens. The ciliary muscles accommodating apparatus is confined by ciliary body 140 and is divided into longitudinal fibers 110, radial fibers 120 and circular fibers 130 each having different orientation and, as a result, contracting in different planes. At the front, the longitudinal fibers 110 attach to the scleral spur 150, whereas the radial 120 and circular fibers 130 attach to the back of the trabecular meshwork 160 and posterior wall of the iris 170. Radial fibers 120 are composed of few thin fibers that contracts during disaccommodation (from near to far focus) to focus far objects by pulling out the equatorial part of the eye's capsular bag of the natural lens. Most of circular fibers 130 run in a circle around the ciliary body 140 concentrically with the root of iris 170. During accommodation, (from far to near focus) their sphincter like action constricts the ciliary ring around the natural lens to act synergistically with longitudinal fibers 110 to pull the ciliary body 140 forward and inward by up to about 0.5 mm to focus near objects. The change of a ciliary body during accommodation and disaccommodation can be observed by high frequency ultrasound biomicroscopy (UBM). Sensor cell 190 for detecting a pressure change or electric filed change is placed at the vicinity of the scleral spur 150 at the side of longitudinal fibers 110 to respond to their contraction with accommodation and relaxation with disaccommodation. Due to complexity of different fibers actions with accommodation and disaccommodation, a careful analysis of sensor cell signal, particularly EMG signal, is required and the inclusion of an independent visualization of the ciliary body movement with accommodation and disaccommodation, for instance by UBM, helps with sensor cell signal identification for accommodation and disaccommodation to communicate between a sensor and adjustable optic by the identification data.

FIG. 2 illustrates a portion 200 of eye anatomy responsible for the accommodation process with implanted corneal implant (corneal inlay) 280 at the cornea 270 and sensor cell 290 at the exterior of longitudinal fibers 210 at the vicinity of scleral spur 250. The FIG. 2 also includes natural lens 240 surrounded by the capsular bag. The ciliary muscles accommodating apparatus is divided into longitudinal fibers 210, radial fibers 220 and circular fibers 230 each having different orientation and, as a result, contracting in different planes.

Figures 3, 4:
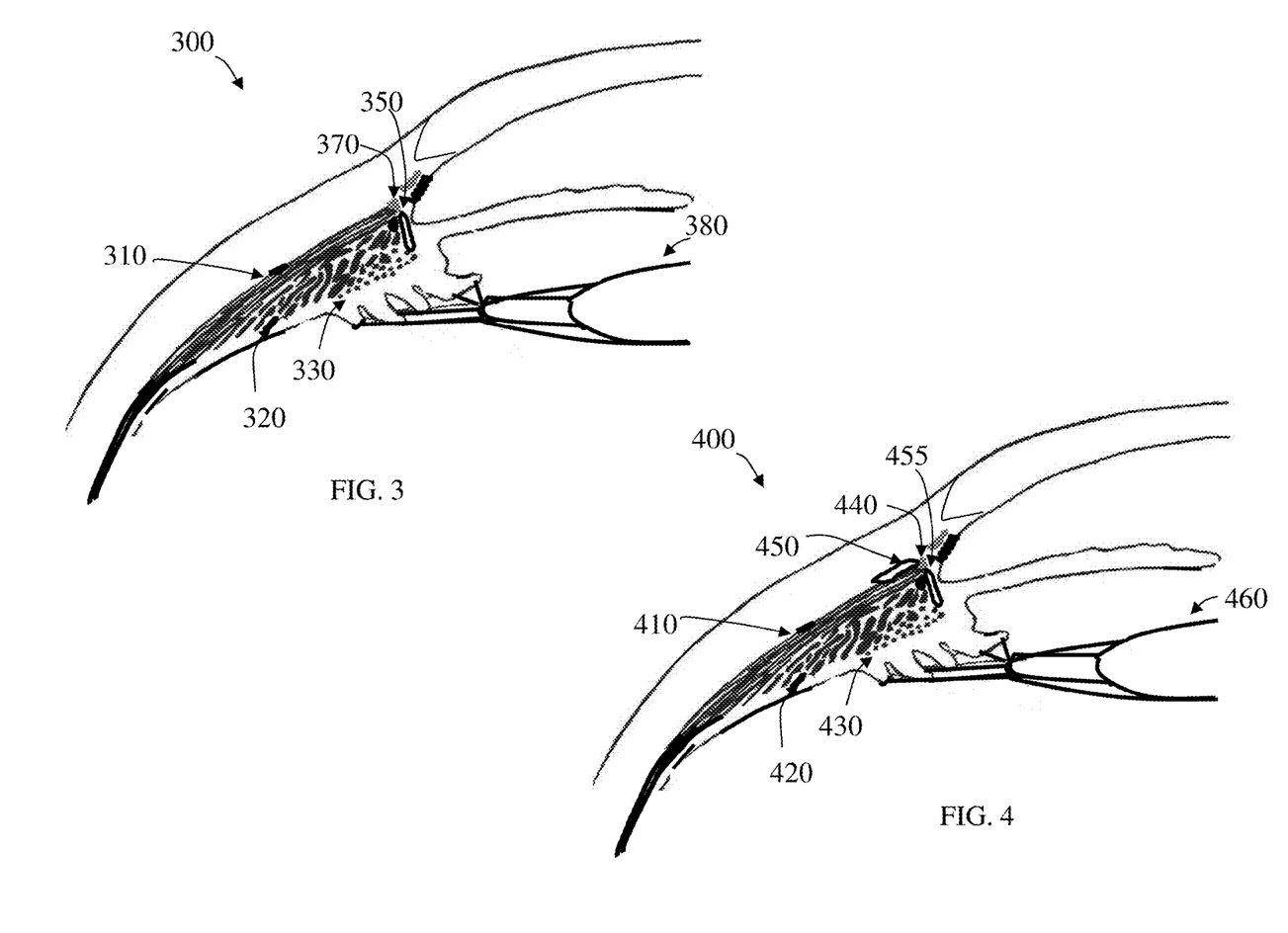
FIG. 3 illustrates a portion of eye anatomy responsible for the accommodation process with implanted aphakic intra-ocular lens and sensor cell at the side of the exterior ciliary muscle where circular fibers are and at the vicinity of the scleral spur.
FIG. 4 illustrates a portion of eye anatomy responsible for the accommodation process with implanted aphakic intra-ocular lens and dual-element sensor cell at both sides next to longitudinal and circular fibers and the scleral spur.

FIG. 3 illustrates a portion 300 of eye anatomy responsible for the accommodation process shown as the eye's cross section. The FIG. 3 includes implanted aphakic intraocular lens 380 that replaces natural lens. The ciliary muscles accommodating apparatus is divided into longitudinal fibers 310, radial fibers 320 and circular fibers 330. Sensor cell 350 is placed at the vicinity of scleral spur 370 at close proximity to circular fibers 330 to respond to their contraction with accommodation and relaxation with disaccommodation.

FIG. 4 illustrates a portion 400 of eye anatomy responsible for the accommodation process shown as the eye's cross section. The FIG. 4 includes implanted aphakic intraocular lens 460 that replaces natural lens. The ciliary muscles accommodating apparatus is divided into longitudinal fibers 410, radial fibers 420 and circular fibers 430. Dual-element sensor cell consists of element 450 that is placed at the vicinity of scleral spur 440 at close proximity to the longitudinal fibers 410 and element 455 also placed at the vicinity of scleral spur 440 at close proximity to the circular fibers 430 to respond to their contraction with accommodation and relaxation with disaccommodation. The elements can be connected by a flexible member. Dual-element sensor cell is useful with its higher response quality which is particularly beneficial for EMG sensor cell.

Figure 5:
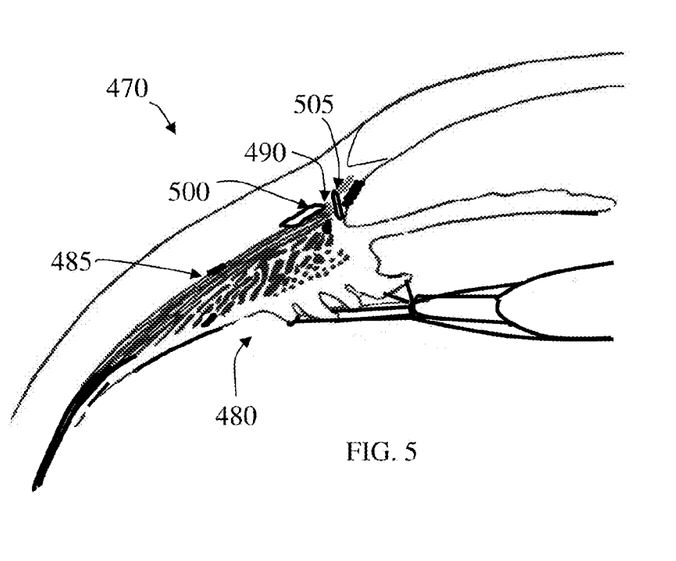
FIG. 5 illustrates a portion of eye anatomy responsible for the accommodation process with implanted aphakic intra-ocular lens and dual-element sensor cell at the opposite sides of the scleral spur with one element being next to the longitudinal fibers.

FIG. 5 illustrates a portion 470 of eye anatomy responsible for the accommodation process shown as the eye's cross section. The ciliary muscles accommodating apparatus is confined by ciliary body 480 and includes longitudinal fibers 485. One element 500 of the dual-element sensor cell is placed at the vicinity of scleral spur 490 at close proximity to longitudinal fibers 485 and another element 505 is placed at the opposite side of the scleral spur 490. The elements can be connected by a flexible member. This dual-element sensor cell is particularly beneficial for pressure sensor cell for differential pressure measurements with ciliary muscles contraction with accommodation when the anterior tendon incorporating the scleral spur 490 is pulled in toward the ciliary muscles thus increasing a pressure on the element 500 and reducing pressure at the element 505. The pulling force drops with disaccommodation thus reducing pressure differential. The dual-element sensor cell might have a different arrangement with one element placed against the circular fibers and another opposite side of the scleral spur.

Figure 6:
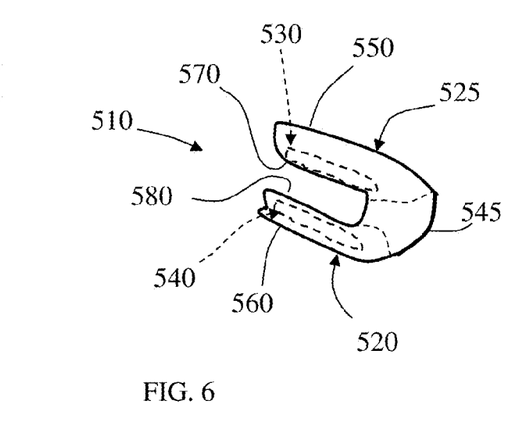
FIG. 6 demonstrates a side view of a dual-element pressure sensor cell for differential signal detection of ciliary muscles actions.

FIG. 6 demonstrates a dual-element pressure sensor cell 510 per this example consisting of two elements 520 and 525 with elastic elements 530 and 540 at each sensor cell element. The elements 520 and 525 of the sensor cell 510 are connected by flexible member 545 and both placed externally and internally to the ciliary muscle fibers with the scleral spur situated closely in between to create a differential pressure between the elastic elements 530 and 540 of the sensor cell 510 with ciliary muscle contraction and relaxation. Each plate 520 and 525 has hard exterior shell 550 or 560 correspondingly and pressure detecting elements 570 or 580 to respond to the force exerted by the ciliary muscle. Mechanical pressure sensor may be similar to an electrostatic (capacitor type) design—mechanical force changes separation between electric plates thus changing an electrical signal of the electronic circuitry though the conversion of the mechanical force into electrical signal or can be based on other designs. For instance, by sandwiching ultrathin gold nanowire between two thin polydimethylsiloxane sheets and flexing the sheets changes the current through the wire. The advantage of such design is that the sensor can resolve pressing, bending, torsional forces and even vibrations to filter the useful signal more precisely.

The pressure differentiation signal is digitized, amplified and electronically processed. It then is converted into ciliary muscle identification data (CMID) corresponding to certain ranges of pressure defined as accommodation and disaccommodation. The CMID is transmitted to the adjustable optic to increase optical power with accommodation or reduce optical power with disaccommodation. It is also possible to have a single element sensor cell to measure absolute pressure changes due to ciliary muscles actions. The elastic element changes its shape due to pressure change which is converted into electrical signal by different principles: electrostatically or variable capacitance, conductivity change due to bending a conducting wire, etc.

Figure 7:
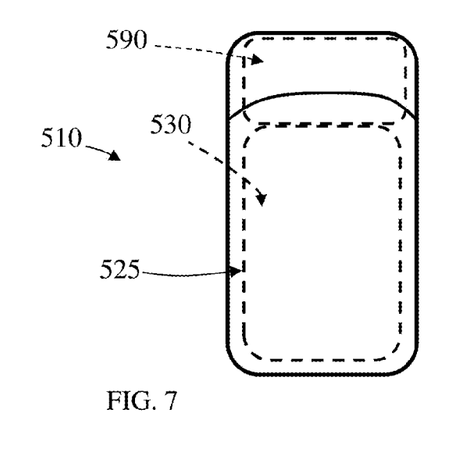
FIG. 7 demonstrates a front view of a dual-element pressure sensor cell for differential signal detection of ciliary muscles contraction and relaxation.

FIG. 7 illustrates sensor cell 510 exterior view facing outside the eye, i.e. front view of the element 525 with the elastic element 530 inside. The electronic part 590 serves for processing and signal transmission and its position within the sensor cell varies. The sensor cell can be of different shape and construction. Dimensionally, there is a benefit to be within dimensions of a glaucoma shunt as the placement of the sensor cell is anatomically close to the common placement of a glaucoma shunt at the trabecular meshwork. The dimensions are about 10 mm width/length and about 2 mm thick which can relate to any type of sensor cell. The dimensions are adequate for planar batteries that have cathodes with thicknesses of up to 5 micron and multiple batteries be placed behind hard exteriors of the sensor cell elements.

Figure 8:
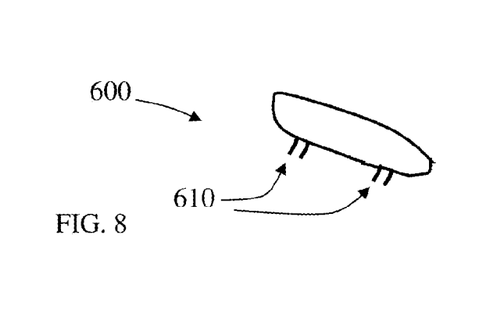
FIG. 8 demonstrates a side view of a one-element EMG sensor cell for electrical field measurements caused by ciliary muscles contraction.

FIG. 8 demonstrates an example of single element EMG sensor cell 600. EMG is a technique in which the electric field characteristic surrounding the muscle is measured. Implantable myoelectric sensors have been developed for surface and intramuscular electromyogram recording. The later is used in the EMG sensor cell. Because the detected electric field is relatively small (in the range of $10^{-4}$-$10^{-3}$V), amplification is used to enhance the electrical signal.

Due to complexity of ciliary muscles activities as some of them are active in disaccommodation (radial fibers) and the majority with accommodation (longitudinal and circular fibers), the conversion of EMG signal into identification data (CMID) is critical. Detailed explanation is provided by FIG. 9. One difficulty with EMG is that electromyographic signals present several interferences that must be removed. Electromyography sensor collects electric samples at high rate, like 1000 Hz in multiple channels. To collect the signals the differential electrodes 610 are use. EMG amplifier is used as a differential amplifier that subtract the value between the electrodes. Electrodes placement is important in relation to muscular fibers, they are placed along the fibers. For instance, if EMG sensor cell is placed against the longitudinal fibers, then the electrodes are along front to back of eye imaginable line (direction of the optical axis of the eye), if against the circular fibers, they are in a plane perpendicular to the optical axis of the eye. In case of EMG dual-element sensor cell, the electrodes in one element are along longitudinal fibers and electrodes in other element are along circular fibers.

Figure 9:
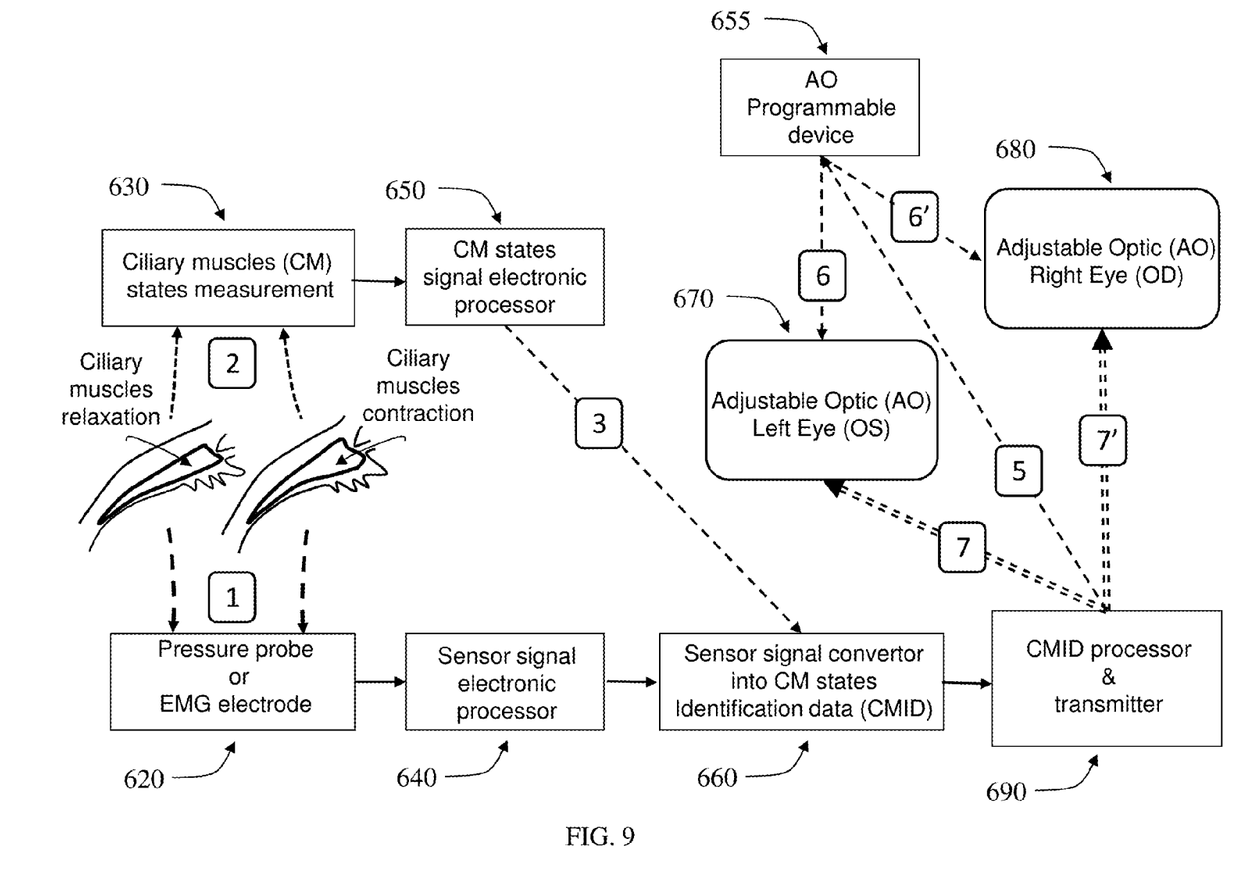
FIG. 9 shows a diagram of a sensor cell process of measuring ciliary muscle contraction and relaxation, ciliary muscle actions visualization and conversion the signal into ciliary muscles identification data corresponding to ciliary muscles ranges of relaxation and contraction and their transmission to adjustable optics.

FIG. 9 illustrates a block diagram of setting up and conducting wireless communication between a sensor cell and adjustable optic. Thus, accommodation for near focus corresponds to contraction of longitudinal and circular fibers of ciliary muscles and disaccommodation to relaxation of the corresponding fibers. The fibers effect on the sensor cell via pressure probes or EMG electrodes is shown by lines 1. Thus, pressure probes or EMG electrodes, block 620, generate electrical signal from the ciliary fibers actions which electronically processed as explained above, block 640. Visual information of the ciliary body contour change during ciliary muscles contraction and relaxation is also collected by UBM (ultrasound biomicroscopy), lines 2. The UBM measures the change in the ciliary body contours as it is known that the ciliary body center of gravity moves forward and inward with fibers contraction during accommodation. The visualization is defined by a change of the center of gravity of the ciliary body contour or by any other parameter associated with the ciliary body contour change. The corresponding electronic signal is called visualization signal. This objective measurement of ciliary fibers action is required because it is the only verifiable way to test for accommodation/disaccommodation in a presbyopic subject.

The visualization device collects the images of ciliary body contours, block 630, processes them into useful electronic visualization signal, block 650. Sensor cell convertor, block 660, collects visualization signal from visualization processor, block 650, as shown by line 3, and together the visualization signal and signal from the sensor cell are time superimposed to general ciliary muscle identification data (CMID). The ranges of visualization signal corresponding to accommodation and disaccommodation are established independently by the scientific analysis. The sensor cell convertor 660 establishes the range of sensor cell signal corresponding to the established visualization signals for accommodation and disaccommodation to generate corresponding ciliary muscle identification data (CMID) that act as the switching signals for an adjustable optic, say "1" signal for disaccommodation and "0" signal for accommodation. Thus, if censor cell transmits signal "0", the adjustable optic switches to higher optical power for near focus, if the signal "1", it switches to lower optical power for far focus. The CMID is transmitted to an adjustable optic for its optical power control as shown by lines 7 and 7' which is also beneficial with commonly used bilateral application of two adjustable optic lenses for left and right eyes. This takes into consideration that ciliary muscles activities for accommodation and disaccommodation are usually equivalent in both eyes and only one sensor cell implantation is required.

As the simplest solution, the same CMID is used for all adjustable optics if NFC technology used with its short reading distance that mitigates safety concerns that a given adjustable optic inadvertently communicates with external signals from other sensor cells. Nevertheless, there is advantage to secure communication against such a possibility. For this purpose a blank programmable RFID tag is included with the adjustable optic. The sensor cell ID is collected either from spec documentation or electronically by the censor cell activation as shown by line 5. The AO (adjustable optic) programmable device 655 collects sensor cell ID and programs both adjustable optics 670 and 680 with the sensor cell ID information, lines 6 and 6'. The data on sensor cell ID is transmitted to identify the adjustable optic for CMID transmission by the sensor cell, lines 7 and 7'.

If NFC technology is used, the NFC-enabled sensor cell initiator/reader in the reading mode initiates NFC-enabled adjustable optic target/transponder, the adjustable optic transponder provides data on sensor cell ID for the censor cell reader to recognize the adjustable optic by the sensor cell with the same ID. The sensor cell than uses P2P mode to pass CMID signal to the adjustable lens to increase its optical power for near focus or reduce its optical power for far focus. An accommodation reflex time is a fraction of second and wireless communication does not present an issue with accommodation respond time.

Adjustable lens may be a phakic intraocular lens, aphakic intraocular lens, corneal implant (inlay), contact lens or spectacle lens. In generally, it is also possible to apply several adjustable lenses to one eye to complement each other power changes, say lens is the ocular implant and another lens is a corneal inlay, contact lens or spectacle lens. Single sensor cell of the present invention that includes identification data is set to communicate with any number of adjustable lenses.

Figure 10:
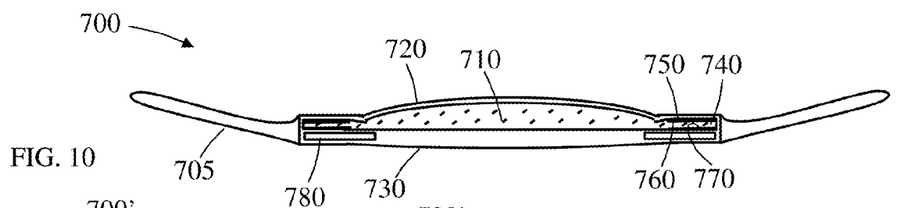
FIG. 10 demonstrates cross-section of dual-chamber fluidic lens activated by electrostatic force directly at the holding chamber. The lens being in relaxed state for far focus when the force is not applied.

FIG. 10 demonstrates dual-chamber fluidic adjustable optic of intraocular lens 700 shaped for a typical aphakic implantation. It includes transparent chamber 710 that effects the optical power of the lens 700 due a change in its shape by the elastic membrane 720 and another, so called holding chamber 740 which shape is controlled by electrostatic force. Both are filled with an optical fluid. The transparent chamber covers the optical aperture of the lens, about 4-6 mm diameter, i.e. it is image forming part of the lens 700. The other side of the transparent chamber 710 is limited by a substrate 730. The holding chamber 740 is an annular shape circumfering the transparent chamber 710 but might be a different shape. Its external diameter is up to about 10 mm leaving some room for supporting member 705 to support the lens inside the eye. At the location of the holding chamber at the substrate there are electronic components 780 of the adjustable optic to communicate with the sensor cell and activate optic for the optical power change. The internal surface of the holding chamber 740 includes conductive coating (Au, $TiO_2$, etc.) 760 and 770 coated with protective coatings for their protection from the optical fluid.

It also could be a wiring to form a conducting surface. The coating 760 is placed on the flexible membrane 750 of the holding chamber. Together, the conductive coatings 760 and 770 act as electrodes to form electrostatic chamber with a dialectic material such as protective coatings and optical fluid between them. The FIG. 1 demonstrates the adjustable lens for far focus when the voltage is not applied to electrodes 760 and 770 and the holding chamber is in the relaxed state.

Figure 11:
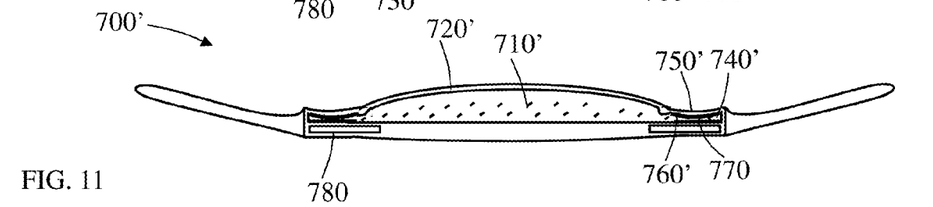
FIG. 11 demonstrates cross-section of two-chamber fluidic lens of FIG. 9 activated by electrostatic force directly at the holding chamber and being in active state for near focus when the force is applied.

FIG. 11 demonstrates the adjustable lens 700' from FIG. 10 in active state for near focus. The electronic component 780 receives a signal corresponding to accommodation and turns on the voltage between electrodes 760' and 770. An electrostatic force between the conductive surfaces of the electrostatic chamber is created when a voltage is applied between the electrodes, $$F = \frac{C}{2 \cdot S} \cdot V^2,$$ Eg. 1

Where S is separation between the electrodes; C is capacitance of the dielectric material between the electrodes (dielectric fluid plus protective coatings); V is applied voltage to the electrodes. The applied voltage creates attracting electrostatic force F between the electrodes that deforms the membrane 750' to push the optical fluid out the holding chamber 740' into the transparent chamber 710' thus making the membrane 720' more curved. The result is a higher optical power of the adjustable lens 700' for near focus. Each lens can be calibrated for a particular voltage to transfer a specific amount of lens optical fluid from holding to transparent chambers required for near focus, say 2-2.5 D Add to allow near focus to be around 50-40 cm from the eye.

As the electronic component 780 receives a signal corresponding to disaccommodation, it turns the voltage off to bring the transparent chamber shape to the configuration for far focus shown on the FIG. 10. The signal from a sensor cell might also be in analog form to continually control the dual-chamber fluidic lens shape, i.e. to continue increasing the optical power to certain level corresponding to a level of the signal from the censor cell that, in turn, is the result of a certain level of the ciliary muscle activity. The central point of the FIGS. 10 and 11 is that dual-chamber fluidic lens allows a practical implementation of such a control.

Figure 12:
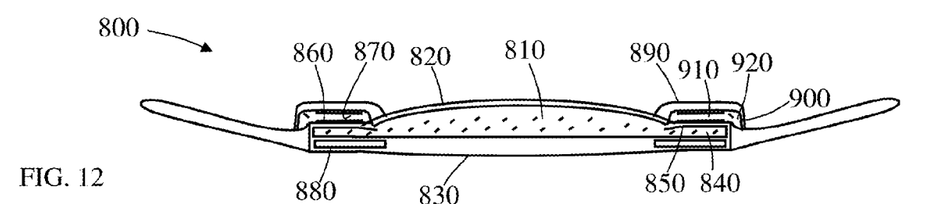
FIG. 12 demonstrates cross-section of dual-chamber fluidic lens activated by electrostatic force indirectly at the holding chamber by applying it to the control chamber and being in relaxed state for near focus when the force is not applied.

FIG. 12 demonstrates dual-chamber fluidic adjustable optic of intraocular lens 800 shaped for a typical aphakic implantation with additional, so called control chamber 910 to indirectly effect the shape of the holding chamber 840. Similar to FIG. 10, it includes transparent chamber 810 that effects the optical power of the lens due a change in its shape by the elastic membrane 820 and holding chamber 840 which shape is controlled by the shape of elastic membrane 850. Transparent and holding chambers are filled with an optical fluid. The transparent chamber 810 is within the optical aperture of the lens, about 4-6 mm diameter, i.e. image forming part of the lens. The other side of the transparent chamber 810 is limited by a substrate 830. The holding chamber 840 is an annular shape circumfering the transparent chamber 810 but might be a different shape. Its external diameter is up to about 10 mm. At the location of the holding chamber within the substrate there are electronic components 880 of the adjustable optic to communicate with the sensor cell and activate optic for an optical power change.

Figure 13:
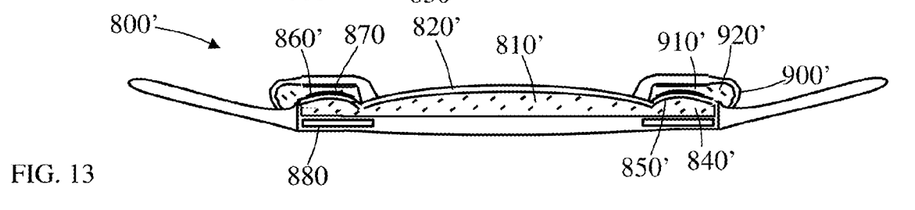
FIG. 13 demonstrates cross-section of dual-chamber fluidic lens of FIG. 12 activated by electrostatic force indirectly at the holding chamber by applying it to the control chamber and being in active state for far focus when the force is applied.

There is a control chamber 910 surrounded by conductive coatings 860 and 870 acting as electrodes of electrostatic chamber. The conductive coating 870 is on non-elastic wall 890 and conductive coating 860 is on the elastic membrane 850 separating control chamber 910 and holding chamber 840. There is also elastic membrane 900, as a continuation of wall 890 in this case to form so called excess chamber 920. Excess chamber 920 and control chamber 910 form a single chamber but they might be separated by a channel. As the control chamber 910 is adjacent to the holding chamber 840, the adjustable lens 800 is shaped for near focus in the resting state when the voltage is not applied to the electrostatic chamber FIG. 13 demonstrates the adjustable lens 800' of FIG. 12 in active state for far focus. The electronic component 880 receives a signal corresponding to disaccommodation and turns on the voltage between conductive coatings 860' and 870. Due to attraction between the conductive coatings, the flexible membrane 850' deforms reducing the volume of the control chamber 910' and increasing the volume of the holding chamber 840' thus transporting a certain amount of optical fluid from the transparent chamber 810' to the holding chamber 840' by flattening membrane 820'. The result is lower optical power of adjustable lens 800' for far focus. The reduced volume of the control chamber 910' forces some amount of dielectric fluid into the excess chamber 920' by deforming the elastic membrane 900'.

As the electronic component 860 receives a signal corresponding to accommodation, it turns the voltage off to bring the transparent chamber shape to the configuration for near focus shown on the FIG. 12.

Figure 14:
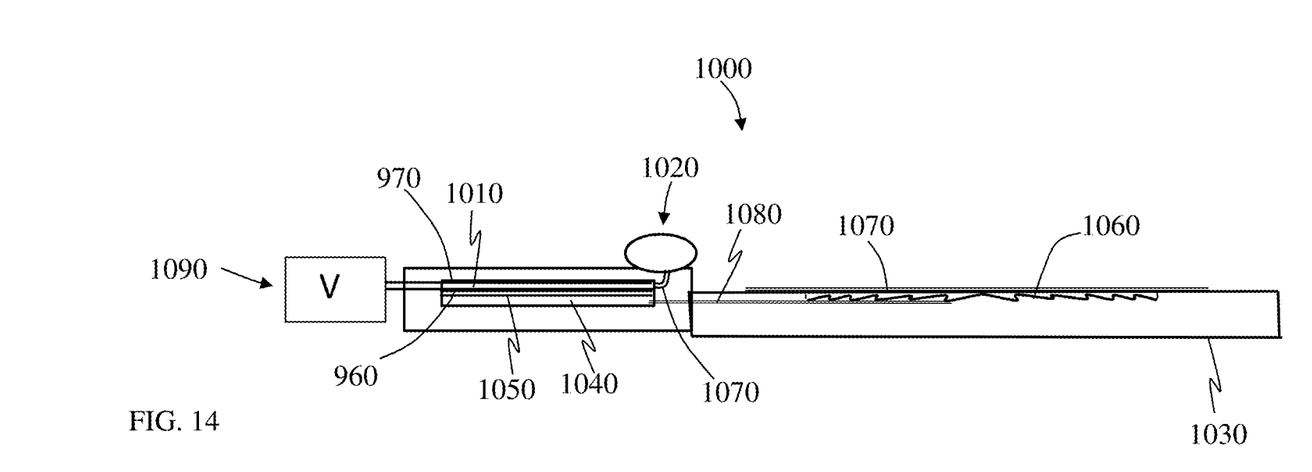
FIG. 14 demonstrates cross-section of RDS optic design activated by electrostatic force indirectly on the holding chamber by applying it to the control chamber and being in relaxed state for far focus when the force is not applied.

FIG. 14 demonstrates the adjustable lens designed for far focus in the relaxed state, i.e. in absence of power (voltage). In addition, it overcomes a need for adjustable optic voltage calibration for required Add power because tolerances of membranes of different chambers involved. The optic shown on the FIG. 14 is switchable optic in which the difference between far and near foci, i.e. Add power, is inherently established by the adjustable optic itself. The U.S. Patent Application Publication No: 2014/0085726 introduced refractive-diffractive switchable (RDS) optical element that acts as opto-mechanical transistor for switching between near and far foci if a pressure is above certain level or below certain level. An RDS optic 1000 of the present invention includes substrate 1030 with diffractive guiding surface 1060 to set the Add power of the RDS optic. The lens includes elastic film 1070 adjacent of the guiding surface to form transparent chamber between the film 1070 and guiding surface 1060 filled with matching optical fluid. The transparent chamber is connected with holding chamber 1040 by channel 1080. The holding chamber 1040 and control chamber 1010 are separate by the elastic membrane 1050, otherwise they are surrounded by non-elastic walls. Internal surfaces of the control chamber 1010 are coated with conductive coatings 960 and 970 which are also coated by protective coating for their protection from the dielectric fluid between them. The conductive coatings 960 and 970 act as electrodes to form electrostatic chamber. The control chamber 1010 is also connected with the excess chamber 1020 by the channel 1070. There is a power source 1090 for the electrodes 960 and 970 controlled by electronic components of the RDS lens 1000. In the absence of voltage, the control chamber 1010, holding chamber 1040 and transparent chamber are all in equilibrium with resting state of the elastic film 1070 with the film 1070 forming refractive surface for far focus.

Figure 15:
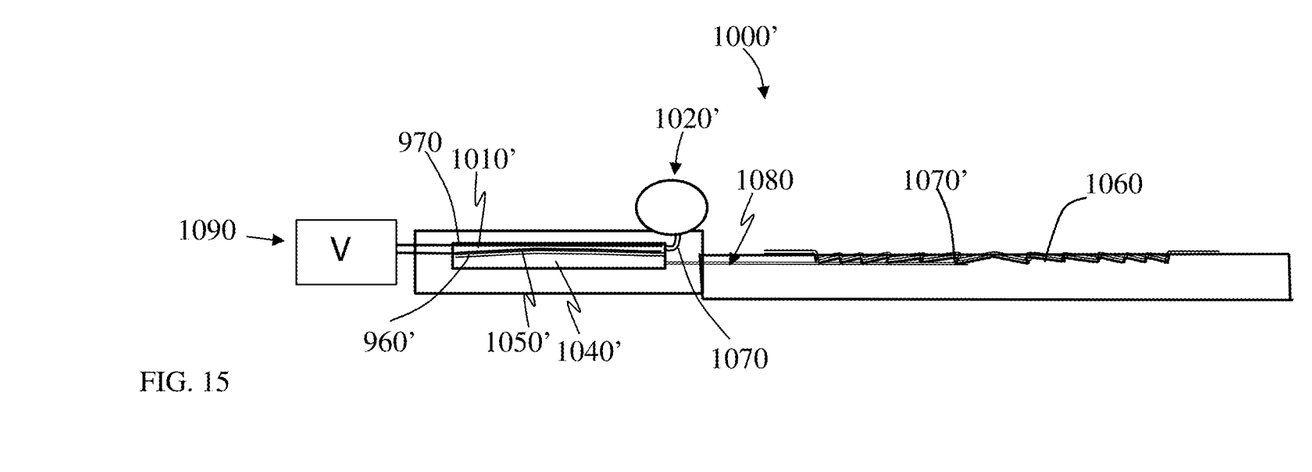
FIG. 15 demonstrates cross-section of RDS optic design of FIG. 14 activated by electrostatic force indirectly on the holding chamber by applying it to the control chamber and being in active state for near focus when the force is applied.

FIG. 15 demonstrates the adjustable optic 1000' of the FIG. 14 in active state for near focus. The electronics of the adjustable optic 1000' receives a signal to switch to higher power for near focus and activates power source 1090 to apply voltage between conducting coatings 960' and 970 of the control chamber 1010'. Due to attracting force between the electrodes 960 and 970, the flexible membrane 1050' deforms thus increasing the volume of the holding chamber 1040'. The balance of dielectric fluid of the control chamber 1010' is pushed into the excess chamber 1020' via the channel 1070. As the holding chamber 1040' volume increases, it pulls in certain amount of matching fluid from the transparent chamber between the guiding surface 1060 and elastic film 1070 via the channel 1080 forcing the film 1070' takes largely the shape of the guiding surface 1060 to manifest the equivalent diffractive surface shape for near focus.

As the electronic component of the adjustable optic 1000' receives a signal corresponding to disaccommodation, it turns the voltage off to bring the elastic film and transparent chamber back into relaxed state for far focus as shown on the FIG. 14.

Although several embodiments have been described in detail for purposes of illustration, various modifications may be made to each without departing from the scope and spirit of the invention. Accordingly, the invention is not to be limited, except as by the appended claims.

What is claimed is:

1. A sensor assembly configured for implantation into, adjacent to or near a portion of a ciliary muscles for a human eye, the sensor assembly comprising:
    a first sensor configured to sense a contraction and relaxation movement of the ciliary muscles producing a range of signals;
    a sensor signal electronic processor in communication with the first sensor, the sensor signal electronic processor configured to process, digitize, and amplify the range of signals;
    a second sensor configured to measure a change in a ciliary body contours of the ciliary muscles;
    a ciliary muscle states signal processor in communication with the second sensor, the ciliary muscle states signal processor configured to process the change in a ciliary body contours of the ciliary muscles into a visualization signal;
    a sensor signal converter in communication with the both the sensor signal electronic processor and the ciliary muscle states signal processor, the sensor signal converter configured to then create a transmittable identification data signal from the range of signals and the visualization signal;
    a transmitter in communication with the sensor signal converter, the transmitter configured to transmit the identification data signal via wireless communication;
    wherein the identification data signal comprises either a first identification state associated with any range of signals corresponding to the contraction movement of the ciliary muscles or a second identification state associated with any range of signals corresponding to the relaxation movement of the ciliary muscles;
    wherein the first identification state is the same value for any range of signals corresponding to the contraction movement and the second identification state is the same value in the range of signals corresponding to the relaxation movement; and
    wherein the first identification state is wirelessly read in by an adjustable optic to change it to a higher optical power for near focus or the second identification state is wirelessly read in by the adjustable optic to change it to a lower optical power for a far focus.

2. The assembly of claim 1, wherein the first sensor comprises a pressure sensor configured to detect a pressure change at the ciliary muscles.

3. The assembly of claim 1, wherein the first sensor comprises an electromyographic sensor configured to detect an electric field change within the ciliary muscles.

4. The assembly of claim 3, wherein the eye comprises ciliary muscles with longitudinal and circular fibers, wherein the electromyographic sensor comprises differential electrodes, the differential electrodes configured to be placed against the longitudinal fibers and/or the circular fibers with an imaginable line closing the electrodes to be generally aligned with the muscle fibers of longitudinal fibers and/or the circular fibers.

5. The assembly of claim 1, wherein the eye comprises ciliary muscles with longitudinal fibers originated at a scleral spur, and the first sensor assembly is configured to be implanted at the vicinity of the scleral spur at the side of the longitudinal fibers.

6. The assembly of claim 1, wherein the eye comprises ciliary muscles with circular fibers and longitudinal fibers originated at a scleral spur, and the first sensor assembly is configured to be implanted at the vicinity of the scleral spur at close proximity to the circular fibers.

7. The assembly of claim 1, wherein the eye comprises ciliary muscles with circular fibers and longitudinal fibers originated at a scleral spur, wherein the first sensor comprises a dual-element sensor connected by a flexible member, wherein a first-side sensor of the dual-element sensor is configured to be placed at the vicinity of scleral spur in close proximity to the longitudinal fibers, and a second-side sensor of the dual-element sensor is configured to be placed at the vicinity of scleral spur in close proximity to the circular fibers.

8. The assembly of claim 1, wherein the eye comprises ciliary muscles with longitudinal fibers originated at a scleral spur, wherein the sensor comprises a dual-element sensor connected by a flexible member, wherein a first-side sensor of the dual-element sensor is configured to be placed at the vicinity of scleral spur in close proximity to the longitudinal fibers, and a second-side sensor of the dual-element sensor is configured to be placed at the generally opposite side of the scleral spur.

9. The assembly of claim 1, wherein the wireless communication comprises a radio-frequency communication.

10. A sensor assembly configured for implantation into, adjacent to or near a portion of a ciliary muscles for a human eye, the sensor assembly comprising:
    a first sensor configured to sense a contraction and relaxation movement of the ciliary muscles producing a range of signals;
    a sensor signal electronic processor in communication with the first sensor, the sensor signal electronic processor configured to process, digitize, and amplify the range of signals;
    a second sensor configured to measure a change in a ciliary body contours of the ciliary muscles;
    a ciliary muscle states signal processor in communication with the second sensor, the ciliary muscle states signal processor configured to process the change in a ciliary body contours of the ciliary muscles into a visualization signal;
    a sensor signal converter in communication with the both the sensor signal electronic processor and the ciliary muscle states signal processor, the sensor signal converter configured to then create a transmittable identification data signal from the range of signals and the visualization signal;
a transmitter in communication with the sensor signal converter, the transmitter configured to transmit the identification data signal via wireless communication;
wherein the identification data signal comprises either a first identification state associated with any range of signals corresponding to the contraction movement of the ciliary muscles or a second identification state associated with any range of signals corresponding to the relaxation movement of the ciliary muscles;
wherein the first identification state is the same value in the range of signals corresponding to the contraction movement and the second identification state is the same value in the range of signals corresponding to the relaxation movement; and
wherein the first identification state is wirelessly read in by an adjustable optic to change it to a higher optical power or the second identification state is wirelessly read in by the adjustable optic to change it to a lower optical power.

11. The sensor assembly of claim 10, wherein the first and second identification state is associated with the change in the range of signals corresponding to the contraction movement or the relaxation movement of the ciliary muscles using the method of visualization of the change in ciliary body contours, the ciliary body center of gravity moving forward and inward with fiber's contraction and the ciliary body center of gravity moving backward and outward with fiber's relaxation.

12. The sensor assembly of claim 11, wherein the visualization comprises ultrasound biomicroscopy.

13. The sensor assembly of claim 10, wherein the sensor signal electronic processor for the sensor assembly is configured to include a sensor ID data with the transmittable identification data signal, and wherein the adjustable optic is configured to accept and change its optical power due to the transmittable identification data signal when the sensor ID data is uniquely recognized by the adjustable optic, and wherein the adjustable optic is configured not to change its optical power due to the transmittable identification data signal when the sensor ID is not recognized by the adjustable optic.

14. The sensor assembly of claim 10, wherein the adjustable optic comprises at least two adjustable optics, both configured to change their optical powers based on the first or second identification states from the same sensor assembly.

* * * * *